United States Patent [19]

Rice et al.

[11] 4,265,229

[45] May 5, 1981

[54] ORAL HYGIENE APPARATUS FOR SHOWERS

[76] Inventors: Harold E. Rice, 1128 Dover Dr.; N. Ray Neel, 1104 Dover Dr., both of Provo, Utah 84601

[21] Appl. No.: 70,781

[22] Filed: Aug. 29, 1979

[51] Int. Cl.³ .............................................. A61H 9/00
[52] U.S. Cl. ...................................... 128/66; 128/229
[58] Field of Search .................. 128/229, 66, 224, 239

[56] References Cited

U.S. PATENT DOCUMENTS

| | | | |
|---|---|---|---|
| 2,507,214 | 5/1950 | Medley | 128/229 |
| 2,550,565 | 4/1951 | Hyser | 128/229 |
| 3,870,045 | 3/1975 | Vaughan | 128/229 |

FOREIGN PATENT DOCUMENTS 567849  3/1945  United Kingdom ...................... 128/229

Primary Examiner—John D. Yasko

[57] ABSTRACT

An oral hygiene apparatus for attachment to a shower head assembly for cleansing the teeth and the oral cavity with a jet stream of water while showering. The apparatus housing is in the form of a hollow valve body which interconnects the shower inlet pipe with the shower head. A hose leading from a needle valve regulated orifice in the valve body connects to a nozzle applicator. The needle valve controls the flow of water into the orifice, through the hose and out the nozzle. The nozzle applicator contains a reservoir for holding a dentifrice, fluoride preparation, breath freshener and the like.

7 Claims, 5 Drawing Figures

ORAL HYGIENE APPARATUS FOR SHOWERS

BACKGROUND OF THE INVENTION

This invention relates to an apparatus for cleaning teeth while in the shower. More particularly, this invention relates to an apparatus which may be attached to a shower between the shower inlet pipe and shower head and which will deliver a jet stream of water into the mouth concomitant with showering.

Various methods and apparatus have been and are being used for cleaning the teeth and oral cavity. The most generally used apparatus is the conventional toothbrush containing a dentifrice in the from of a paste or gel. Of recent years apparatus have also been developed for applying a jet of water against the teeth. This method is often preferably to the use of a brush when cleaning teeth containing orthodontic appliances. A jet stream of water is often able to penetrate crevices and spaces between teeth and orthodontic appliances which cannot be reached by a brush thereby dislodging food particles and plaque which would otherwise not be removed. A problem associated with the use of either a tooth brush or a water jet dispenser is that a mirror, basin, walls and other areas adjacent thereto often become covered with water, toothpaste or particles that splatter from the open mouth during the cleaning process. As a result dentists see many people, teenagers with orthodontic appliances in particular, who avoid cleaning their teeth properly because it is a time consuming and messy procedure. Moreover, many water jet type of appliances fall into disuse because of the water splash problem and the necessity to clean up each time the appliance is used.

OBJECTS AND BRIEF DESCRIPTION OF THE INVENTION

It is therefore an object of the present invention to provide an apparatus for efficiently cleaning the teeth and oral cavity in general by a jet stream of water while taking a shower, thereby eliminating problems of water splashing and clean-up.

It is also an object of the present invention to provide an apparatus for cleaning teeth by a jet stream of water in a shower wherein the water flow and pressure through the apparatus and into the mouth may be regulated by means of a needle valve.

Another object of the invention is to provide an apparatus for cleaning teeth in a shower by a jet stream of water wherein the applicator nozzle may contain a dentifrice, fluoride, breath freshener, mouthwash, medicament or other material which may become mixed with the water passing through the applicator and applied to the mouth in the jet stream.

These and other objects may be accomplished by means of an apparatus in the form of a valve positioned intermediate the shower head and shower inlet pipe. The valve is threaded so as to thread onto the inlet pipe and into the shower head thereby becoming easily attachable to any conventional shower. The valve consists of a hollow body forming a water passageway from the inlet pipe to the shower head. An orifice is contained in the lateral side of the valve body at the bottom. A nipple or lip, which is integral with the valve body, surrounds the orifice on the outside of the valve and protrudes downwardly forming a hose connection. On the inside of the valve and surrounding the orifice is a circular or conoidal seat. In the valve body wall exactly opposite the orifice and in alignment therewith is a threaded aperture through which is threaded a valve needle having a circular pointed or conoidal end which seats into the area surrounding the orifice when the needle is threaded across the water passageway thereby sealing the orifice. The opposite end of the valve needle outside the valve body containsan enlarged end or knob which aids in turning the needle with the fingers.

A hose is connected at one end to the protruding nipple and at the other to an applicator having a spray nozzle. The applicator has an enlarged barrel like reservoir portion adjacent the hose connection adapted to hold a chemical composition such as a dentifrice, mouthwash, breath freshener, fluoride preparation and the like. The spray or jet nozzle is located at the end of the barrel portion opposite the hose connection.

The apparatus is operated in the shower by first turning on the shower to the desired temperature and then opening the valve needle a sufficient distance to provide for the correct amount of water and pressure leaving through the orifice and passing, via the hose through the applicator nozzle and into the mouth of the user.

DRAWINGS

DETAILED DESCRIPTION OF THE INVENTION

There is shown in FIGS. 1–5 a complete embodiment of the invention.

Figure 1:
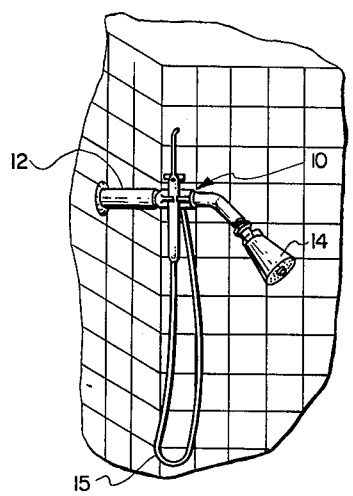
FIG. 1 is a fragmentary perspective view of a shower having the apparatus of the present invention attached thereto.
Figure 2:
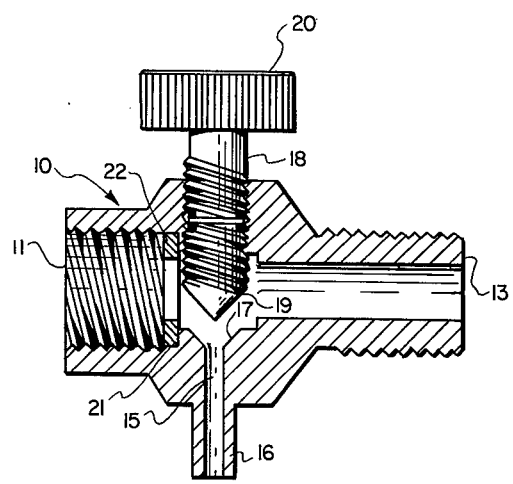
FIG. 2 is a longitudinal cross section of the valve illustrated in FIG. 1 showing the operational function of the needle valve.
Figure 3:
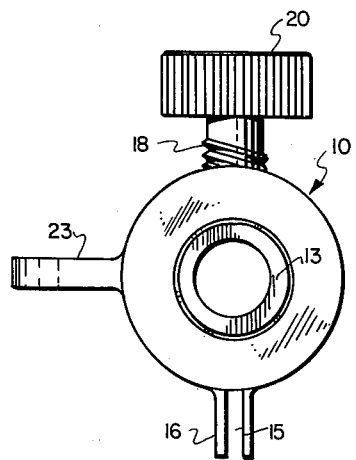
FIG. 3 is a front end view of the valve illustrated in FIG. 1.
Figure 4:
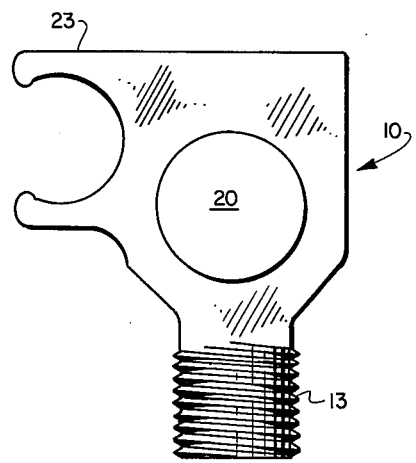
FIG. 4 is a top view of the valve illustrated in FIG. 1.

FIG. 1 shows in perspective the apparatus completely assembled in a shower and ready for use. The apparatus as shown in FIGS. 1 and 2 consists of an open hollow valve body 10 internally threaded at one end 11 for attachment to a shower inlet pipe 12 and outwardly threaded at the opposite end 13 for attachment of a shower head 14 thereon. The lateral sidewalls may be of uniform thickness or may be thicker in the central section intermediate ends 11 and 13 as shown in FIG. 2. An orifice 15 extends through one lateral sidewall and is of lesser diameter than the diameter of the main longitudinal passageway. A nipple 16, which is integral with the lateral sidewall, surrounds the orifice on the outside of the valve body 10 and forms an extension thereof. The nipple serves as a hose connection as will be more completely described hereinafter. The area immediately surrounding the orifice at the inside of the lateral sidewall is beveled to form a circular or conoidal seat 17. In the lateral sidewall opposite the orifice 15 and in alignment therewith a threaded aperture into which is inserted a threaded valve needle 18. The inner end 19 of the valve needle 18 is pointed to conoidal and dimensioned to engage firmly into seat 17 and seal orifice 15. The outer end of valve needle 18 contains a knob 20 to facilitate the threading of the valve needle across the hollow valve body. The valve needle 18 may be configured to be surrounded by an O ring or other sealing means. With the valve needle 18 firmly seated into valve seat 17 the orifice is sealed; however, by turning the knob 20 the valve nose 19 will be retracted from the valve seat 17 allowing water to be diverted from the hollow valve body and through the orifice 15.

As also shown in FIG. 2 the longitudinal passageway through valve body 10 is preferably stepped i.e., from a ½" ID to a ⅜"ID, thereby forming a step or seat 21 for seating a ring gasket 22 which seals the valve body 10 to the inlet pipe 12 when engaged thereon.

While not essential to the operation of the present invention, the valve body also preferably contains attaching means 23 as an integral part of the valve body for securing the oral hygiene applicator 24 thereto when not in use as will be more fully described.

Figure 5:
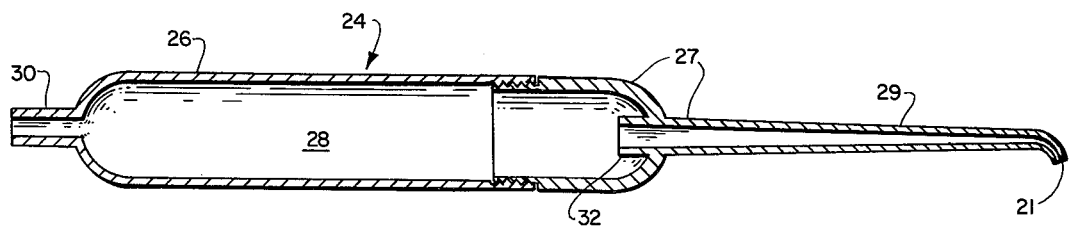
FIG. 5 is a longitudinal cross section of one embodiment of an oral hygiene applicator suitable for use in the present invention.

A hose 25 is stretch fitted over nipple 16 and may be further secured by means of clamps if desired. The hose 25 is of sufficient length to be freely moved about in the shower by the user for the intended purpose. At the opposite end of hose 25 is the applicator 24. While any suitable applicator may be used the one illustrated in FIG. 5 is particularly useful. This applicator consists of two detachable pieces 26 and 27 which, when connected, form a lower barrel shaped cylindrical reservoir portion 28 and an upper nozzle portion 29. The two pieces interconnect along the barrel portion by means, e.g., interlocking threads, such that access is provided into the reservoir 28 for the addition of a dentifrice, mouthwash, breath freshener, fluoride preparation or other water soluble or dispersible composition thereto. The lowermost portion of applicator 24 consists of a hollow nipple 30 which serves as a hose connection and provides access for incoming water into the reservoir 28. The reservoir is of greater diameter than the nozzle and also serves as a handle for the applicator. The nozzle 29 is generally cylindrical and is located at the opposite end of the reservoir from the nipple 30. The nozzle tapers to a smaller diameter as it extends away from the reservoir and terminates in an orifice of a size predetermined to emit therefrom an appropriate jet stream of water. The tip 31 of the nozzle is preferably curved so as to terminate in a plane some 30 to 90 degrees from the longitudinal axis of the barrel and nozzle thereby making it easier for the user to direct the water jet into the desired position in the mouth.

The mouth 32 of the nozzle, preferably extends a small distance into the reservoir. This encourages mixing of chemical compositions within the reservoir by creating turbulence therein. Thus, materials placed in the reservoir, such as dentifrices, will be dissolved or suspended and enter the nozzle mouth from within the interior of the reservoir rather than being forced out the extreme end of the reservoir chamber, where larger undissolved or unsuspended particles may accumulate.

Various materials may be placed within the reservoir simply by disconnecting parts 26 and 27 and adding the desired amount of substance to the open reservoir chamber. Dentifrices, mouthwashes, breath fresheners, antiseptics, disinfectants, fluoride preparations or any other types of oral preparations, which are either water soluble or suspendible may be added to the reservoir.

The holder 23 on the valve body is preferably shaped to have two extending arms forming a semicircle in between adapted to functionally engage and hold the barrel like reservoir portion of the applicator 24 as illustrated in FIG. 1. The holder 23 may be positioned such that the applicator may be either vertical or horizontal when engaged.

The apparatus is preferably assembled so that the orifice 15 in the valve body 10 is pointed downward with the needle valve knob 20 forming the uppermost top of the assembly. In other words the needle valve is in a vertical position. However, other positions, such as the needle valve being horizontal may also be used, and any terminology, such as top or bottom, when referring to position is deemed to include all operable positions.

The apparatus is intended to be used only when the user is showering and thus no attempt is made to prevent water from passing through the shower head when using the oral hygiene applicator. The apparatus is preferably stored with the valve needle engaged in the valve seat sealing orifice 15. When using the apparatus, the shower is first adjusted to the proper temperature any desired dentifrice or other substance has been added to the applicator, the valve needle is rotated by the user to emit the proper amount of water through applicator nozzle 29 and out through tip 31 in the form of a jet spray. The jet of water is directed into the mouth and against the teeth thereby dislodging food particles, plaque and other foreign materials. This method is particularly beneficial in cleaning teeth containing braces or other forms of orthodontic appliances. There is no need to worry over water splashing and therefore a more thorough and rigorous cleaning process may be carried out than is possible at a bathroom basin or sink.

Although the invention as has been described is deemed to be that which would form the preferred embodiment thereof, it is recognized that departures may be made therefrom and still be within the scope of the invention which is not to be limited to the details disclosed but is to be accorded the full scope of the claims and any and all equivalent devices and apparatus.

We claim:

1. An oral hygiene apparatus adapted to be interconnected between a water outlet pipe and a shower head which comprises,
    (a) a hollow valve body open at each end for passing water from said outlet pipe to said shower head,
    (b) a lateral bottom opening in said valve body for diverting water away from said shower head having valve seating means in the inside of the valve body at said opening and an outwardly protruding nipple on the outside of said valve body surrounding the lateral bottom opening and forming a continuation thereof,
    (c) a valve needle threaded through the valve body opposite the lateral bottom opening and extending into said hollow valve body, said valve needle having a pointed inner end adapted to seat into said valve seating means and seal the lateral bottom opening when said valve needle is threaded completely across said hollow valve body and adapted to control the pressure and amount of water passing through said lateral bottom opening when said valve needle is threaded away from said seating means and into the hollow portion of the valve body without preventing the flow of water to said shower head said valve needle also containing an enlarged outer end outside said valve body to facilitate turning of said needle valve;
    (d) hose means connected to said outwardly protruding nipple and (e) an oral hygiene applicator attached to the opposite end of said hose said applicator.

2. An oral hygiene apparatus according to claim 1 wherein the oral hygiene applicator has a lower enlarged barrel portion forming a reservoir adjacent the hose means adapted to hold a dental hygiene composition and an upper nozzle end adapted to convey a jet of water containing said dental hygiene composition into the mouth of a person using said appliance.

3. An oral hygiene apparatus according to claim 2 wherein the oral hygiene applicator consists of two detachable interconnectable pieces such that, when detached, an acces into the barrel portion for placement of the dental hygiene composition therein is provided.

4. An oral hygiene apparatus according to claim 3 wherein the nozzle portion of the oral hygiene applicator extends into the reservoir of the barrel portion such that water entering the nozzle portion does not come directly from the end of the reservoir.

5. An oral hygiene apparatus according to claim 2 wherein the valve body contains attachment means adapted to receive and hold the barrel portion of the oral hygiene applicator in a fixed position.

6. An oral hygiene apparatus according to claim 5 wherein said attachment means are positioned laterally on said valve body and extend outwardly in a plane which is at right angles from the valve needle.

7. An oral hygiene apparatus according to claim 6 wherein the attachment means consists of two outwardly extending flexible arms adapted to engage the barrel portion of the oral hygiene applicator.

* * * * *